US008387347B2

(12) United States Patent
Imai et al.

(10) Patent No.: US 8,387,347 B2
(45) Date of Patent: Mar. 5, 2013

(54) PROCESS FOR PRODUCING AND STERILIZING A CATHETER

(75) Inventors: Yukio Imai, Fujinomiya (JP); Takashi Suzuki, Fujinomiya (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 205 days.

(21) Appl. No.: 12/788,975

(22) Filed: May 27, 2010

(65) Prior Publication Data

US 2010/0251669 A1 Oct. 7, 2010

Related U.S. Application Data

(62) Division of application No. 11/795,601, filed as application No. PCT/JP2006/300805 on Jan. 20, 2006, now abandoned.

(30) Foreign Application Priority Data

Jan. 21, 2005 (JP) ................................ 2005-014081

(51) Int. Cl.
*B65B 55/08* (2006.01)

(52) U.S. Cl. ............ 53/425; 53/426; 604/48; 604/93.01

(58) Field of Classification Search .................... 53/425, 53/426; 604/48, 93.01
See application file for complete search history.

(56) References Cited

U.S. PATENT DOCUMENTS 3,477,474 A 11/1969 Mesler
4,301,803 A 11/1981 Handa et al.
4,813,210 A * 3/1989 Masuda et al. .................. 53/425
4,882,113 A 11/1989 Tu et al.
5,147,315 A 9/1992 Weber
6,127,486 A 10/2000 Bürger et al.
6,897,245 B2 5/2005 Gen
2002/0022825 A1 2/2002 Saitou et al.
2002/0139785 A1 10/2002 Peacock, III et al.
2005/0045184 A1* 3/2005 Khera et al. .................. 128/831
2006/0230476 A1 10/2006 Atanasoska et al.
2007/0005003 A1* 1/2007 Patterson et al. ............... 604/43

FOREIGN PATENT DOCUMENTS

EP 1 270 660 1/2003
JP 5-271430 A 10/1993
JP 6-223637 A 8/1994
JP 10-179754 A 7/1998
JP 2000-225194 A 8/2000
JP 2001-161824 A 6/2001
JP 2001-178814 A 7/2001
JP 2001-190681 A 7/2001
JP 2003-695 A 1/2003

OTHER PUBLICATIONS

International Search Report issued by the Japanese Patent Office as the International Searching Authority in International Application No. PCT/JP2006/300805 dated Feb. 14, 2006.

(Continued)

*Primary Examiner* — Thanh Truong
(74) *Attorney, Agent, or Firm* — Buchanan Ingersoll & Rooney PC

(57) ABSTRACT

A process for producing a catheter comprises mixing ETFE and PTFE in a mass ratio of from 99:1 to 45:55 to form a mixture, forming the mixture into a tubular body, forming a reinforcement layer and a resin layer on said tubular body to form a catheter configured to be positioned in a lumen of a living body, sealingly packaging the catheter to produce a packaged catheter, and sterilizing the packaged catheter with electron beam irradiation.

20 Claims, 4 Drawing Sheets

OTHER PUBLICATIONS

International Preliminary Report on Patentability issued by the Japanese Patent Office as the International Searching Authority in International Application No. PCT/JP2006/300805 dated Jul. 24, 2007.

Written Opinion issued by the Japanese Patent Office as the International Searching Authority in International Application No. PCT/JP2006/300805.

Extended European Search Report issued Mar. 13, 2009 in EP Patent Application No. 06 71 2030.3, EPO, The Hague, NL.

Minosio, J.-P., et al., Absence d'interaction chimique entre des cathéters courts (ETFE) et trois antibiotiques majeurs. Modèle d'étude., *Ann. Pharmaceutiques francaises*, 1994 (month unknown), vol. 52, No. 6, pp. 303-310, Elsevier Publishing, Paris, FR, with English abstract.

* cited by examiner

PROCESS FOR PRODUCING AND STERILIZING A CATHETER

This application is a divisional of U.S. application Ser. No. 11/795,601 filed on Jul. 19, 2007, since abandoned, which is a U.S. national stage application of International Application No. PCT/JP2006/300805 filed on Jan. 20, 2006 and which claims priority to Japanese Application No. 2005-014081 filed on Jan. 21, 2005, the entire content of both of which is incorporated herein by reference.

TECHNICAL FIELD

The present invention relates to a catheter for medical use to be used for diagnosis or therapy by being inserted into a blood vessel or other body lumen, and to a process for producing the catheter.

BACKGROUND DISCUSSION

In recent years, catheters have been being used in an increasing number of diagnostic and/or therapeutic methods for alleviating the physical and time-basis burdens on patients. Generally, for insertion of a catheter into a living body through a blood vessel, ureter, trachea, esophagus or the like and bringing the catheter accurately to a predetermined site in the living body without damaging the blood vessel wall, organs or the like, the catheter must meet the structural requirements for high operationality and safety when serving as a medical device and, simultaneously, the luminal internal surface of its tube (referred to also as "catheter body") must exhibit lubricity.

The lubricity is necessary for externally injecting a liquid medicine or the like to a predetermined site in the patient's body through the lumen of the catheter body, for draining a body fluid in the living body or the like, or for passing other therapeutic device therethrough.

As a catheter which meets such structural requirements and further has lubricity at the luminal internal surface of a catheter body, for example Patent Document 1 describes a catheter including a catheter body having an outer layer and an inner layer, the outer layer having a first region and a second region located on the proximal end side of the first region, wherein the first region is composed of a polyester elastomer, and the second region is composed of a polyurethane elastomer higher in hardness than the polyester elastomer constituting the first region. This catheter is excellent in operationality such as pushability, torque transmitting property, following property, and anti-kinking property. Besides, in the catheter, a material capable of reducing the friction of an internal surface of the inner layer, for example, a fluorinated resin such as polytetrafluoroethylene (PTFE) is used as the material constituting the inner layer, so that the luminal internal surface of the catheter body has lubricity.

There are many examples in which a fluorinated resin, particularly, PTFE is thus used as the material constituting the luminal internal surface of the catheter body.

Meanwhile, a catheter must be sterilized before used, since it is used for a living body, like other medical devices. General sterilization methods include the methods in which a gas or water vapor is used. These methods, however, have problems as to the toxicity of the gas, the long treatment time required for sterilization, etc.

In view of these problems, the sterilizing method using radioactive rays such as electron beams have come to be paid attention to. According to this method, toxicity is obviated and the treatment time required for sterilization is short.

However, the sterilization method using radioactive rays cannot be applied to the above-mentioned catheters using PTFE.

This is because PTFE is deteriorated when irradiated with ionizing radiations of not less than 1 kGy, and is extremely deteriorated in mechanical properties at an absorbed dose of around 25 kGy, which is a sterilizing dose generally used in the cases of sterilization with γ-rays, electron beams and the like.

For example, when the radioactive-ray sterilization is applied to the catheter described in Patent Document 1 in which PTFE is used to form the inner layer, PTFE is conspicuously lowered in breaking elongation and, therefore, mere bending of the catheter body would result in exfoliation or cracking of the inner layer.

Patent Document 1: Japanese Patent Laid-open No. 2001-190681

Disclosed here is a process for producing a catheter that includes a catheter layer having a luminal internal surface consisting of a material that has lubricity substantially identical with that of PTFE and has a resistance to radioactive rays not had by PTFE.

A process for producing a catheter as disclosed here involves mixing ETFE and PTFE in a mass ratio of from 99:1 to 45:55 and forming the mixture into a tubular body, forming a reinforcement layer and a resin layer on the tubular body obtained and forming a catheter, sealingly packaging the catheter, and sterilizing the packaged catheter with radioactive rays.

The luminal internal surface of the catheter disclosed here has a lubrication characteristic substantially identical with that of PTFE. Therefore, the use of the catheter makes it possible to easily carry out injection externally a liquid medicine or the like to a predetermined site in a patient's body through the lumen of the catheter body, drainage of a body fluid or the like present in the living body, and passage of other therapeutic devices therethrough. In addition, the luminal internal surface of the catheter is composed of a material having a resistance to radioactive rays not had by PTFE. Therefore, a sterilizing method using radioactive rays, which obviates toxicity and ensures that the treatment time required for sterilization is short, can be applied to the catheter disclosed here.

BRIEF DESCRIPTION OF THE DRAWING FIGURES

DETAILED DESCRIPTION

Now, the catheter disclosed here is described below based on preferred embodiments shown in the accompanying drawings.

Figure 1:
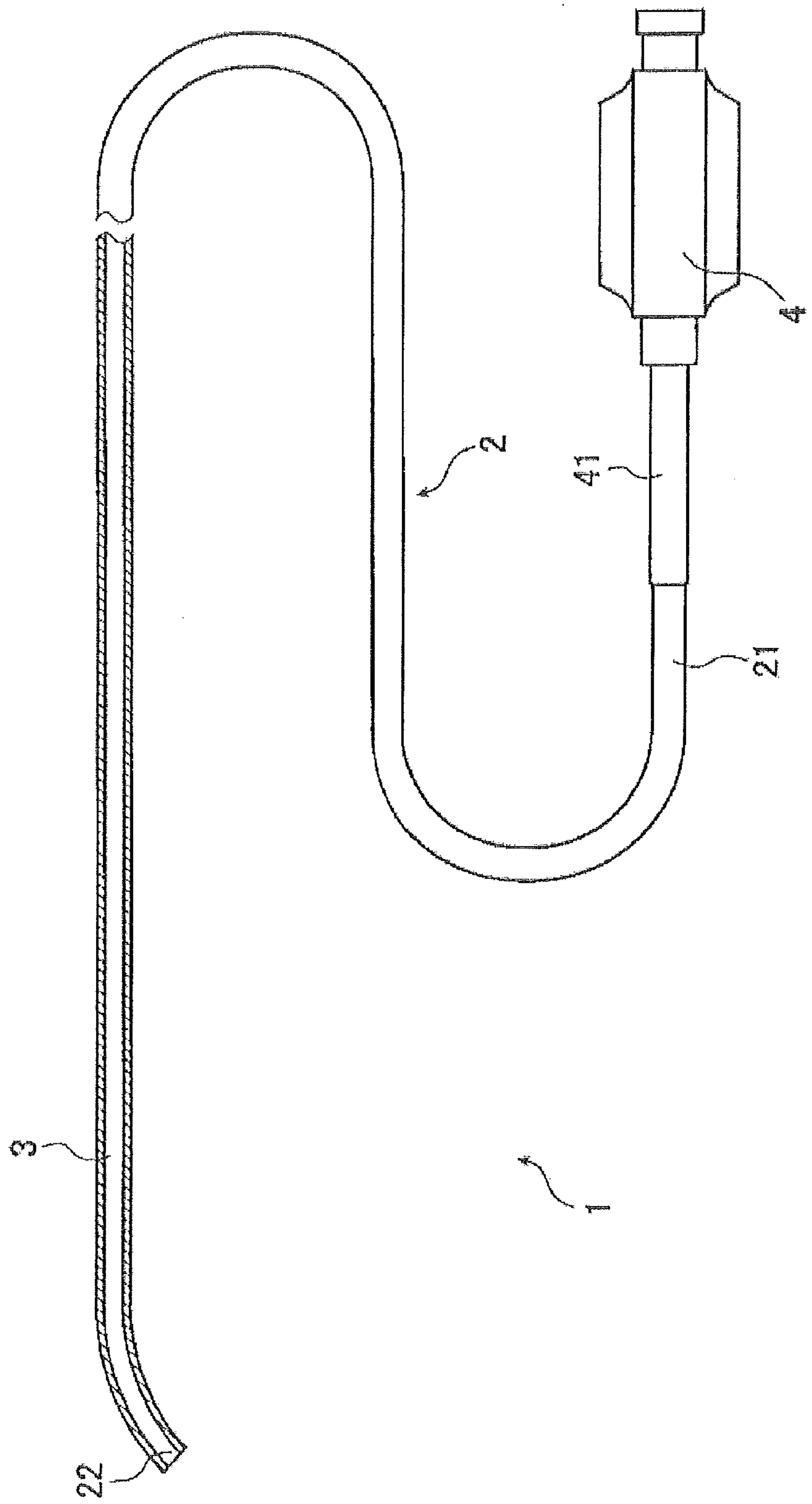
FIG. 1 illustrates an embodiment of overall configuration in the case where the catheter disclosed here is applied to a blood vessel catheter.

FIG. 1 is a plan view showing an example of overall configuration in the case where the catheter disclosed here is applied to a blood vessel catheter. A tip section which is inserted in a lumen such as a blood vessel is shown in section. Hereinafter, the right side in FIG. 1 will be referred to as "the proximal end", and the left side as "the distal end".

The catheter 1 shown in FIG. 1 is composed of a catheter body 2, a hub 4 mounted to the proximal end 21 of the catheter body 2, and an anti-kinking protector 41.

The catheter body 2 is formed with a lumen (i.e., inner cavity) 3 in the inside thereof ranging from the proximal end 21 to the distal end 22. At the time of inserting the catheter 1 into a blood vessel, a guide wire is inserted in the lumen 3. In addition, the lumen 3 can be used also as a passage for a liquid medicine or the like.

The hub 4 functions as an insertion port for inserting the guide wire into the lumen 3, an injection port for injecting a liquid medicine or the like into the lumen 3, and the like, and functions also as a grip section to be gripped at the time of operating the catheter 1.

The overall length of the catheter body, the thickness of the tube wall and the like in the catheter disclosed here are not particularly limited, and can be appropriately selected according to the purpose of use of the catheter.

For example, in the case of a preferred embodiment of the catheter 1 shown in FIG. 1, the overall length of the catheter body (tube) is 800 to 1500 mm, and the thickness of the tube wall is 0.02 to 0.5 mm.

As for the hub 4, common hubs can be used.

In the above-mentioned catheter disclosed here, the catheter body has a catheter layer composed of a composition containing ETFE and PTFE in a mass ratio of from 99:1 to 45:55 (the composition hereinafter referred to also as "the composition disclosed here").

The ETFE used here is not particularly limited, and may be any of those conventionally used widely in the production of medical devices such as catheters. The ETFE can be prepared by copolymerizing TFE (tetrafluoroethylene) with ethylene by a conventionally known method.

The TFE/ethylene polymer composition of the ETFE used here is not particularly limited. In addition, the ETFE may contain a small amount of a third ingredient in such a range as not to spoil the characteristics aimed at here in addition to TFE and ethylene in the composition.

In the ETFE generally widely utilized, the TFE/ethylene polymer composition is from about 50/50 to 60/40 mol %, and the ETFE is substantially an alternate copolymer. Besides, for solving the generation of stress cracking based on its crystallinity, the ETFE contains a third ingredient as follows. Namely, the ETFE generally widely utilized is a ternary copolymer containing the third ingredient. Furthermore, the ETFE has an MFR (melt flow rate: fluidity in a molten state) of 3 to 45 g/10 min, and a density of 1.70 to 1.75 $g/cm^3$.

In the catheter disclosed here, the ETFE thus generally utilized widely can be preferably used.

Examples of the third ingredient includes fluorinated α-monoolefin, fluorinated vinyl ether, hydrofluorocarbon fluorinated vinyl ether, hydrocarbon fluorinated vinyl ether monomer, and vinyl esters.

The PTFE used here is not particularly limited, and may be any of those conventionally used widely in the production of medical devices such as catheters. The PTFE can be prepared by polymerizing the TFE (tetrafluoroethylene) monomer by a conventionally known method.

The PTFE has a melt viscosity of 5,000 to 100,000 poise, and a density of 2.13 to 2.22 g/cm3.

The forms of the ETFE and the PTFE used here are not particularly limited, but these materials are each preferably in a pellet form or a powdery form (a dry powder or a dispersion (a uniform dispersion of a fine powder in a solvent)). It is preferable that the ETFE and/or the PTFE is in a pellet form or a powdery form, since they can be easily mixed with each other.

In addition, where the ETFE and/or the PTFE is in the form of a dispersion, a further homogeneous dispersed state of finer PTFE particles can be obtained, which is preferable from the viewpoint of the possibility that a catheter with a smaller tube wall thickness (1 to 40 μm) can be easily obtained. Dry powdery ETFE and PTFE are commercially available as molding powders and fine powders, and these powders can be preferably used here.

In the catheter layer of the catheter disclosed here, a composition containing the ETFE and the PTFE in a mass ratio of from 99:1 to 45:55, preferably from 95:5 to 60:40, more preferably from 90:10 to 80:20 is applied as the material.

The relationship between the mixing ratio of the ETFE with the PTFE and the resistance to radioactive rays is considered to depend on which of the ETFE and the PTFE forms the sea phase in the sea-island structure upon mixing of the ETFE with the PTFE. Specifically, it is considered that the resistance to radioactive rays is exhibited with priority in the case where the ETFE having a resistance to radioactive rays has a greater volumetric ratio than the PTFE having a higher lubricity; it means that the ETFE forms the sea phase.

The luminal internal surface of the catheter body produced from the composition disclosed here containing the ETFE and the PTFE in the above-mentioned ratio exhibits a high resistance to radioactive rays without loosing the general lubricity characteristic.

Therefore, the use of the catheter here makes it possible to easily carry out external injection of a liquid medicine or the like to a predetermined site in a patient's body through the lumen of the catheter body, drainage of a humor or the like present in the living body, and passage of other medical devices therethrough. In addition, a sterilizing method using radioactive rays which obviates toxicity and ensures that the treatment time required for sterilization is short can be applied to the catheter disclosed here.

Incidentally, the radioactive rays herein includes γ-rays, electron beams, X-rays and the like, and is not particularly limited, insofar as the rays can be used for sterilization of medical devices.

The irradiating temperature and the irradiation dose of the rays are not limited, and may be at the levels which are commonly applied in sterilization of medical devices. For example, the atmosphere for irradiation is room temperature (about 23° C.), and the irradiation dose is 1 to 100 kGy, preferably 15 to 60 kGy.

In addition, the mass ratio of the ETFE to the PTFE is within from 99:1 to 55:45, more preferably from 95:5 to 70:30 in the composition disclosed here such that the composition has a fluidity optimal for injection molding and extrusion molding and is excellent in processibility.

Besides, the composition may contain other organic material(s), in addition to the ETFE and the PTFE.

Examples of the organic material(s) include polystyrene, polyethylene, polyamide, polyimide, polysulfone, polyphenylene sulfide, polyvinyl chloride, polycarbonate, acrylonitrile-styrene copolymer, acrylonitrile-butadiene-styrene copolymer, polyvinyl, silicone, tetrafluoroethylene-hexafluoropropylene copolymer, tetrafluoroethylene-perfluoroalkyl vinyl ether copolymer, polyvinylidene fluoride, polyvinyl fluoride, and ethylene-chlorotrifluoroethylene copolymer.

The composition may also contain the organic material(s) in a proportion of 0.1 to 10 mass % based on the total mass of the ETFE and the PTFE.

Besides, the composition here may contain additives, in addition to the ETFE and the PTFE.

Examples of the additives include pigments, dyes, X-rays contrast agent (barium sulfate, tungsten, bismuth oxide or the like), reinforcing agent (glass fiber, carbon fiber, talc, mica, clay mineral, potassium titanate fiber, or the like), filler (carbon black, silica, alumina, titanium oxide, metal powder, wood flour, rice hull, or the like), thermal stabilizer, oxidation/deterioration inhibitor, UV absorber, lubricant, mold release agent, crystalline nucleophile, plasticizer, flame retardant, antistatic agent, and foaming agent.

The composition here may contain the additive(s) in a proportion of 1 to 50 mass % based on the total mass of the ETFE and the PTFE.

The catheter layer of the catheter body of the catheter disclosed here is produced from the above-mentioned composition by a method which will be described later.

The catheter may have the catheter layer serving alone as the catheter body; however, it is preferable for the catheter to have a resin layer composed of a resin composition different from the composition on the catheter layer. This ensures effectively that the rigidity of the catheter body is enhanced, and the pushability and torque transmitting performance of the catheter body are enhanced.

In addition, when the catheter has such as the resin layer constituting an outer layer, it is effectively ensured that the reinforcement layer to be described later can be firmly fixed within the catheter body.

The resin composition constituting the resin layer is not particularly limited, but it is preferably a resin composition more flexible than the catheter layer (i.e., inner layer). Examples of the resin composition include polyamide resin, polybutylene terephthalate, polyester elastomer, polyethylene terephthalate, and mixtures and copolymers thereof. Among these resin compositions, preferred are polyamide resin and polyester elastomer, in view of their excellent resistance to radioactive rays and little lowering in mechanical properties upon irradiation with radioactive rays.

Examples of the polyamide resin include nylon 6, nylon 66, nylon 610, nylon 46, nylon 9, nylon 11, nylon 12, and nylon 12 elastomer. Among these polyamide resins, preferred are nylon 12 and nylon 12 elastomer, in view of their excellent flexibility and chemical resistance.

The thickness of the resin layer is not particularly limited. Usually, the thickness is preferably about 0.01 to 1.0 mm, more preferably about 0.03 to 0.1 mm.

The resin layer can be formed on the catheter layer, by a method which will be described later.

Further, it is preferable to provide a reinforcement layer between the catheter layer and the resin layer. This ensures effectively that the rigidity of the catheter body is further enhanced, and the pushability and torque transmitting performance of the catheter body are further enhanced.

The reinforcement layer is composed, for example, a spiral element.

The spiral element may be composed of at least one of a metallic member and a nonmetallic member. Examples of the spiral element include those obtained by forming a metallic wire or plate member into a spiral shape, those obtained by forming a nonmetallic string or plate member into a spiral shape, and those obtained by forming a laminate of a metallic member and a nonmetallic member into a spiral shape.

Examples of the material constituting the metallic member include stainless steels, nickel-titanium alloys, platinum, iridium, and tungsten, which may be used either singly or in combination of two or more of them.

On the other hand, examples of the material constituting the nonmetallic member include carbon, polyamide, polyethylene terephthalate, and polybutylene terephthalate, which may be used either singly or in combination of two or more of them.

The pitch of winding of the spiral element is not particularly limited. For example, the pitch is preferably about 0 to 2 mm, more preferably about 0.02 to 0.5 mm. Where the pitch of winding of the spiral element is in such a range, an appropriate rigidity is imparted to the catheter body, and the pushability and torque transmitting performance of the catheter body are further enhanced.

In addition, the cross-sectional shape of the spiral element is not limited to circle, and may be a flat shape; namely, the spiral element may be ribbon-like (i.e., belt-like) in shape.

Where the cross-sectional shape of the spiral element is a circle, the diameter of the circle is preferably about 0.03 to 0.06 mm, more preferably about 0.04 to 0.05 mm.

Where the spiral element is ribbon-like in shape, the width of the ribbon-like shape is preferably about 0.1 to 1.0 mm, and the thickness is preferably about 0.04 to 0.05 mm.

Incidentally, the reinforcement layer is not particularly limited, insofar as it can impart an appropriate rigidity to the catheter body. For example, the reinforcement layer may be composed of the spiral element alone, a braided element alone, or a combination of a braided element and the spiral element (for example, one which is composed of a braided element on the proximal end side and of the spiral element on the tip side, one which is a laminate of a braided element and the spiral element, or the like).

Where a braided element is used, the braided element may be composed of at least one of a metallic member and a nonmetallic member. Examples of the braided element include those obtained by braiding metallic wires alone, those obtained by braiding nonmetallic strings alone, and those obtained by braiding a metallic wire with a nonmetallic string.

Examples of the material constituting the metallic wire include stainless steels and nickel-titanium alloys, or the like, which may be used either singly or in combination of two or more of them.

On the other hand, examples of the material constituting the nonmetallic string include carbon, polyamide, polyethylene terephthalate, and polybutylene terephthalate, which may be used either singly or in combination of two or more of them.

The reinforcement layer composed of such a spiral element or braided element provides a sufficient reinforcing effect even when comparatively small in thickness. Therefore, the catheter body having such a reinforcement layer is advantageous in adopting a smaller diameter.

In the disclosure here, the catheter layer is produced by using the composition containing the ETFE and the PTFE and, optionally, the organic material(s) and/or the additive(s).

The process for producing the catheter layer is not particularly limited; for example, the catheter layer is produced by the following process.

After the pellet form or powdery form ETFE and the powdery PTFE are mixed under stirring, the mixture is fed into a melt extruder, and is stirred at a temperature of 230 to 280° C.

Figure 5:
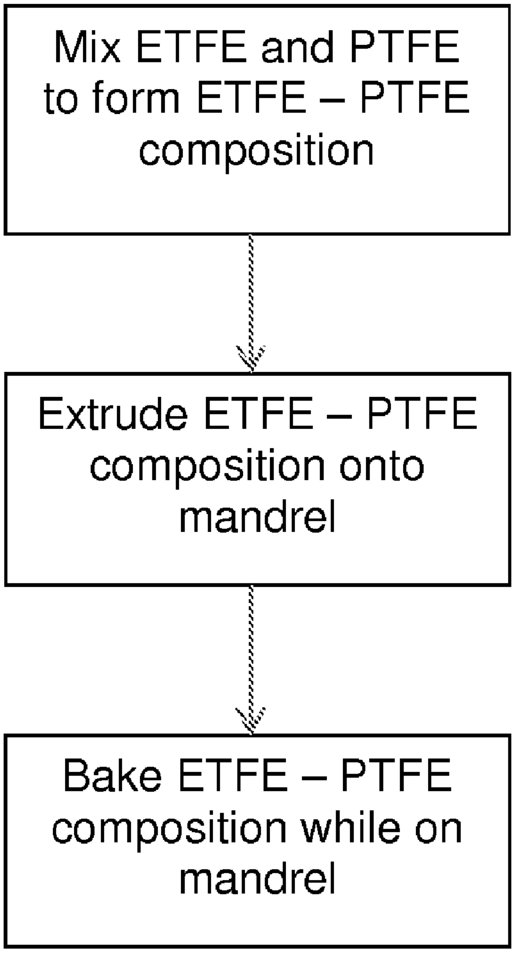
FIG. 5 is a flow chart illustrating process steps to form a catheter layer.

The stirred mixture is extruded by the extruder onto a mandrel to form a coating film, which is subjected to baking together with the mandrel in a furnace, as shown in FIG. 5. The baking temperature should be not lower than the melting point of ETFE, namely, not lower than 220° C. In addition, the baking temperature is preferably not higher than 330° C., which is the melting point of PTFE, and is preferably not higher than 250° C.

Then, the mandrel is drawn out, whereby a round tubular molded article can be obtained as the catheter layer.

Here, when a small amount of a volatile oil (kerosene or the like) is added at the time of mixing the ETFE and the PTFE under stirring, a lumpy composition can be obtained by compressing the stirred composition, which is preferable since the supply of the composition into the extruder and the coating of the mandrel with the composition are stabilized.

The catheter layer produced by such a process as above can be used alone as the catheter body. However, in the case where the reinforcement layer is further formed on the catheter layer, the above-mentioned metallic wire or nonmetallic string is wound therearound at the above-mentioned pitch at a time after the coating of the mandrel with the composition disclosed here by the above-mentioned process and before the baking in a furnace or at a time after the baking in the furnace and before the detaching of the coating film from the mandrel. In the case where the winding is conducted before the baking, the baking is conducted after the winding.

In the case where the resin layer is further formed on the catheter layer produced by the above process or on the reinforcement layer formed as above-mentioned, the composition disclosed here is coated on the mandrel by the above-mentioned process, baked in a furnace, and the reinforcement layer is formed on it. Thereafter, a resin composition as a material for forming the resin layer is applied on the reinforcement layer by use of a melt extruder. Incidentally, the baking may be conducted after the reinforcement layer is formed. In addition, the baking step may be omitted.

Alternatively, a hollow tube is preliminarily formed by extrusion molding using the resin composition prepared as the material for forming the resin layer. Then, the hollow tube is covered with on the thing which composed with the mandrel coated with the composition by the above-mentioned process and the reinforcement layer formed on it. Then, a heat-shrinkable tube composed of a fluorinated resin (e.g., FEP) is fitted over the hollow tube, and the assembly is passed through a heat tunnel (about 340° C.) over a predetermined time (about 10 min), whereby the catheter layer formed of the composition disclosed here, the reinforcement layer, and the resin layer are adhered to each other. Thereafter, the heat-shrinkable tube is peeled off, and the mandrel is drawn out, whereby the catheter body having the reinforcement layer and the resin layer can be produced.

A hub and an anti-kinking protector are attached by an ordinary method to the catheter body produced by the above-mentioned process, whereby the catheter disclosed here can be configured. Further, the catheter is sealed with a packaging material having a barrier property with respect to bacteria, followed by radiation sterilization (preferably, electron-beam sterilization), to complete the production of the catheter disclosed here.

By use of the producing process disclosed here, it is possible to obtain a catheter composed of a material which has lubricity substantially identical with that of PTFE while having a resistance to radioactive rays not had by PTFE. Therefore, it is possible to produce a catheter having been subjected to a radiation sterilizing treatment which obviates toxicity and ensures that the treatment time required for sterilization is short.

In addition, the use of the catheter disclosed here is not particularly limited. For example, the catheter disclosed here can be applied to guiding catheters, angiographic catheters, various balloon catheters for PTCA, PTA, IABP, etc., ultrasonic catheters, atherectomy catheters, endoscopic catheters, indwelling catheters, medical solution injection catheters, and embolism catheters (micro catheters) introduced into an organ such as brain, liver, etc.

EXAMPLES

Now, specific examples of the catheter disclosed here and the results of various tests will be described below.

<Production of Catheter Body>

Catheter bodies corresponding to Examples disclosed here and Comparative Examples were produced by the method described below.

First, ETFE and PTFE powders were mixed for a sufficient time in each of the mass ratios given in Table 1 below, to obtain uniform mixtures. Thereafter, the mixed powders were supplied into a melt extruder so that the compositions disclosed here in a molten state are prepared. The melting temperature was 250° C.

A copper wire (circular in section with 0.65 mm diameter) as a mandrel was mounted into the melt extruder, and melt extrusion at a controlled extrusion rate was conducted, to form a 0.04 mm-thick coating of the composition on the mandrel.

The coated mandrel with the composition was fed continuously into a furnace (referred to a "continuous furnace"). The temperature in the continuous furnace was controlled to 225° C. The baking time in the continuous furnace was about five minutes.

Then, after cooling at room temperature, the mandrel was drawn out, to obtain a catheter body composed solely of a catheter layer. The catheter bodies thus obtained had an overall length of about 1,000 mm, a tubular section, an inside diameter of 0.65 mm, and an outside diameter of 0.73 mm.

<Tensile Test>

From each of the catheter bodies having an overall length of about 1,000 mm produced by the above method, a specimen of about 80 mm in length was carved out, and was irradiated with electron beams by use of an electron beam irradiation system (Rhodotron T-300 model, produced by IBA located in Belgium) so that the absorbed dose would be 33 kGy.

Thereafter, the specimens were held at room temperature (23±3° C., 50% RH) for four weeks, and then they were subjected to a tensile test (according to JIS K7113). Here, the tensile test speed was 100 mm/min, and the chuck-to-chuck distance was 50 mm.

The measurement results of tensile strength by the tensile test are shown in Table 1, and the measurement results of breaking elongation are given in Table 2. Incidentally, the results of measurement for specimens not irradiated with electron beams are also shown. Furthermore, the results given in Table 1 are shown also in FIGS. 2 and 3.

TABLE 1

| Composition (mass %) ETFE | PTFE | Tensile strength (A) before irradiation (gf) | Tensile strength (B) after irradiation with electron beams (gf) | Retention ratio of tensile strength (B/A) (%) |
|---|---|---|---|---|
| 100 | 0 | 959 | 872 | 91 |
| 90 | 10 | 557 | 521 | 94 |
| 85 | 15 | 488 | 452 | 93 |
| 80 | 20 | 358 | 341 | 95 |
| 60 | 40 | 370 | 311 | 84 |
| 50 | 50 | 420 | 195 | 47 |
| 44 | 56 | 430 | 187 | 43 |
| 40 | 60 | 480 | 161 | 34 |
| 20 | 80 | 540 | 122 | 23 |
| 0 | 100 | 634 | 104 | 16 |

TABLE 2

| Composition (mass %) ETFE | PTFE | Breaking elongation (A) before irradiation (%) | Breaking elongation (B) after irradiation with electron beams (%) | Retention ratio of toughness (B/A) (%) |
|---|---|---|---|---|
| 100 | 0 | 253 | 261 | 100 |
| 90 | 10 | 439 | 435 | 99 |
| 85 | 15 | 142 | 150 | 100 |
| 80 | 20 | 58 | 56 | 97 |
| 0 | 100 | 620 | 4 | 0.6 |

Figure 2:
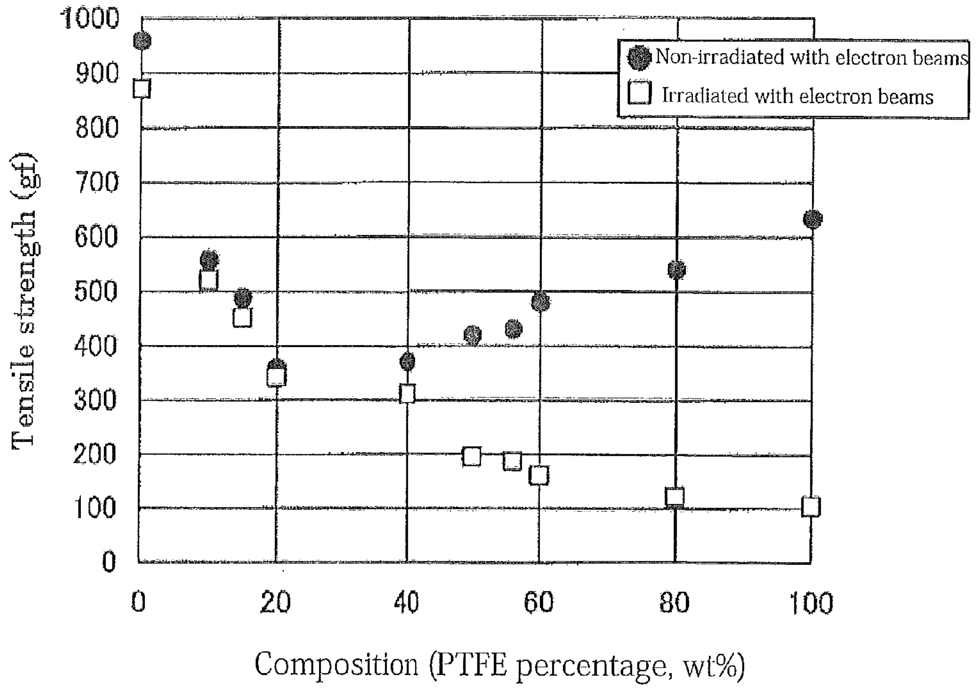
FIG. 2 is a diagram showing the relationship between PTFE blending proportion and tensile strengths before and after irradiation with electron beams.
Figure 3:
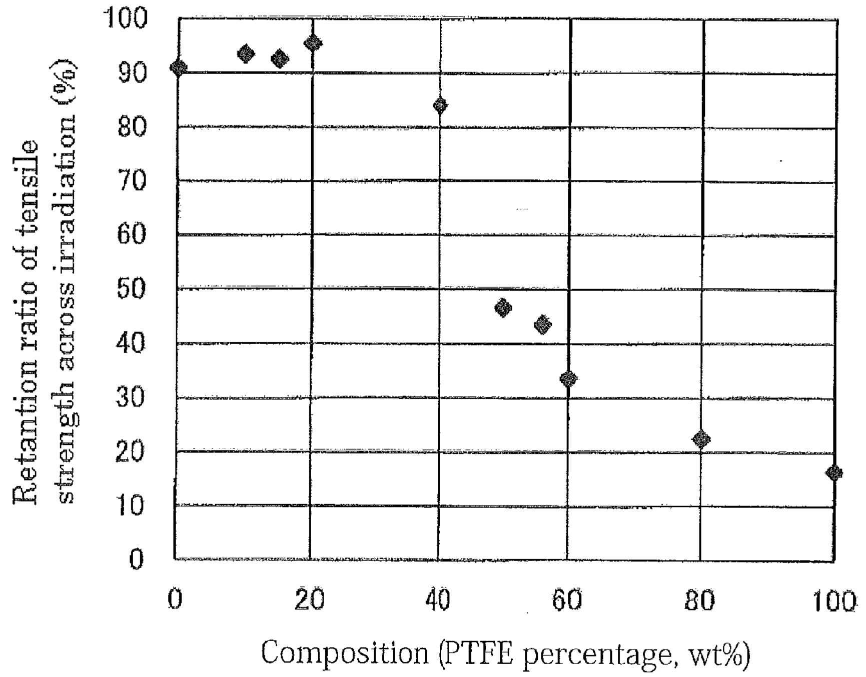
FIG. 3 is a diagram showing the relationship between PTFE blending proportion and the retention of tensile strength before and after irradiation with electron beams.

From FIGS. 2 and 3, it is seen that where the ratio of PTFE is not less than 40 mass %, a conspicuous difference in tensile strength is generated between the case of irradiation with electron beams and the case of not conducting the irradiation.

The reason is considered to be as follows. As has been above-mentioned, where ETFE is present in an amount of not less than 45 mass %, the ETFE forms the sea phase, whereby the deterioration of strength by irradiation with electron beams can be suppressed. Where ETFE is present in an amount of about 45 to 60 mass %, the effect disclosed here may partly not be exhibited. On the other hand, where the ETFE is present in an amount of not less than 60 mass % (namely, where PTFE is present in an amount of less than 40 mass %), the effect on the whole is exhibited sufficiently.

The shaft strength of the distal section was also measured by a method similar to that for the tensile test. The shaft strength of the distal section means the tensile strength of a flexible part in the range of about 100 mm from the distal end of the catheter.

Incidentally, as the catheter body, two compositions were respectively used, one corresponding to ETFE/PTFE=80/20, and the other corresponding to ETFE/PTFE=0/100. For each of these compositions, a specimen irradiated with electron beams and a non-irradiated specimen were subjected to the test, for comparison.

The results of the test are shown in Table 3.

TABLE 3

| Composition (mass %) ETFE | PTFE | Irradiation with electron beams | Shaft strength of the distal section (gf) | Retention ratio of strength (%) |
|---|---|---|---|---|
| 80 | 20 | Non-irradiated | 517 | 89.2 |
| | | Irradiated | 461 | |

TABLE 3-continued

| Composition (mass %) ETFE | PTFE | Irradiation with electron beams | Shaft strength of the distal section (gf) | Retention ratio of strength (%) |
|---|---|---|---|---|
| 0 | 100 | Non-irradiated | 831 | 23.6 |
| | | Irradiated | 196 | |

The retention ratio of the shaft strength of the distal section (the ratio of the shaft strength of the electron beam-irradiated specimen to that of the non-irradiated specimen) in the case of ETFE/PTFE=80/20 was about 90%, which is apparently advantageous over the case of ETFE/PTFE=0/100.

<Accelerated Ageing Test>

In the same manner as in the above tensile test, an about 80 mm clipped specimen was got from the main body of the catheter which produced about 1,000 mm full length by the process mentioned above, and it was irradiated with electron beams by use of an electron beam irradiating system (Rhodotron T-300 model, produced by IBA located in Belgium) so that the absorbed dose would be 33 kGy.

Then, each of the specimens was put in a warm air circulation type oven (product code: STAC P-500M, produced by Shimadzu Corporation) for 168 hours. The temperature inside the oven was set to 60° C.

Thereafter, each of the specimens was cooled at room temperature (2313° C., 50 RH) for 24 hours, and then subjected to the same tensile test as above.

The results are shown in Table 4.

TABLE 4

| Composition (mass %) ETFE | PTFE | Tensile strength after irradiation with electron beams (gf) | Breaking elongation after irradiation with electron beams (%) |
|---|---|---|---|
| 100 | 0 | 850.8 | 265 |
| 90 | 10 | 515.5 | 408 |
| 85 | 15 | 452.6 | 148 |
| 80 | 20 | 321.6 | 46 |

<Lubricity Test>

Figure 4:
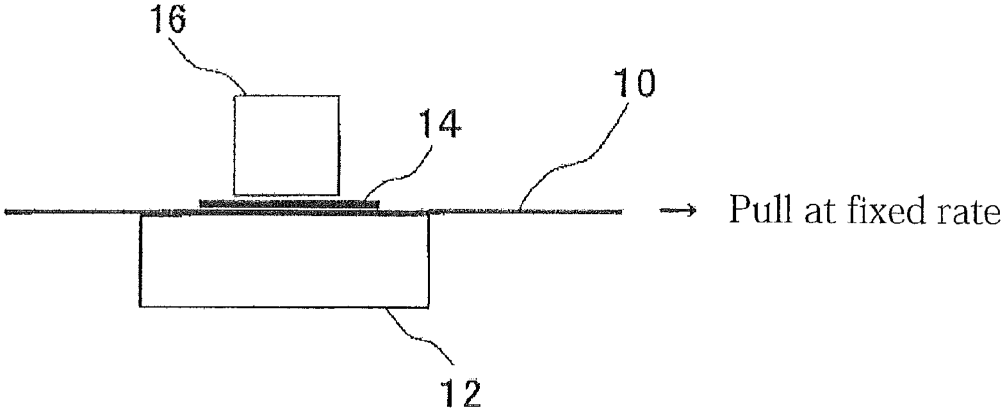
FIG. 4 is a schematic illustration of a measuring instrument for friction test of a material forming the catheter body disclosed here.

The catheter bodies disclosed here and produced by the above process were subjected to measurement of frictional resistance (i.e., coefficient of static friction and coefficient of dynamic friction), by the following method. FIG. 4 shows a schematic illustration of the measurement.

Each of the catheter bodies having an overall length of about 1,000 mm produced by the above-mentioned process was pressed down in a diametral direction to form a rectangular parallelepiped piece of about 500 mm×1.2 mm×0.08 mm, which was used as a specimen 10.

The specimen 10 is mounted on a smooth table 12 (made of SUS304) having a sufficiently large area and kept horizontal, a PTFE sheet 14 (30×30 mm, 0.5 mm thickness) is mounted on the specimen 10, and a 200-g weight 16 is mounted on the PTFE sheet 14. Here, the weight 16 is put on the PTFE sheet 14 without protruding from the area of the PTFE sheet 14, and a contact area between the PTFE sheet 14 and the specimen 10 is about 36 mm2. In addition, a contact area (i.e., sliding area) between the specimen 10 and the smooth table 12 is also about 36 mm2.

Then, the specimen is pulled horizontally at a fixed rate of 100 mm/min by use of a testing machine (Autograph AG-IS, produced by Shimadzu Corporation) capable of measuring tensile load.

Here, the coefficient of static friction was calculated from the tensile load immediately before the specimen 10 started moving. Besides, the coefficient of dynamic friction was calculated from the tensile load measured as a fixed value after the specimen 10 started moving.

The results of the test are shown in Table 5.

TABLE 5

| Composition (mass %) | | Coefficient of static friction | Coefficient of dynamic friction |
|---|---|---|---|
| ETFE | PTFE | (F/W) | (F/W) |
| 100 | 0 | 0.220 | 0.192 |
| 90 | 10 | 0.257 | 0.235 |
| 85 | 15 | 0.355 | 0.308 |
| 80 | 20 | 0.435 | 0.380 |
| 0 | 100 | 0.640 | 0.400 |

F: Measured load, W: Press-down load

<Internal Surface Sliding Test>

Each of the catheter bodies having an overall length of 1,000 mm produced by the above-mentioned process was fixed in a U shape. Here, the curved portion of the U shape had an overall length of 160 mm and a radius of curvature of 50 mm.

A diagnostic guide wire (commercial name: Radifocus Guidewire, produced by TERUMO CORPORATION) or a spring type guide wire (produced by ASAHI INTECC CO., LTD.) was inserted into the lumen of the catheter body from its one end.

Then, the guide wire was fixed at its end part to a chuck of the same tensile testing machine as used above and reciprocatory slid. Accordingly, the internal surface sliding resistance was measured.

The results are shown in Table 6.

TABLE 6

| Composition (mass %) | | Irradiation with | Internal surface sliding resistance (gf) | |
|---|---|---|---|---|
| ETFE | PTFE | electron beams | vs. GW * 1 | vs. SW * 2 |
| 80 | 20 | Non-irradiated | 4.68 | 5.58 |
| | | Irradiated | 4.80 | 5.38 |
| 0 | 100 | Non-irradiated | 4.76 | 8.12 |
| | | Irradiated | 5.00 | 12.50 |

* 1: Diagnostic guide wire
* 2: Spring type guide wire

It was found that the catheter body with ETFE/PTFE=80/20 according to the disclosure here exhibits an internal surface sliding property comparable to or better than that of a catheter body with ETFE/PTFE=0/100.

What is claimed is:

1. A process of manufacturing and packaging a catheter comprising:

manufacturing a catheter body comprised of a catheter layer, a reinforcement layer and a resin layer, the catheter layer being made of a composition that includes both ETFE and PTFE in a mass ratio of 99:1 to 45:55, the catheter body being tubular in form and possessing a wall thickness of 0.02 mm to 0.5 mm, the catheter body possessing a proximal end;

forming the reinforcement layer so the reinforcement layer is positioned in overlying relation to the catheter layer;

forming the resin layer outside the reinforcement layer so that the reinforcement layer is positioned between the catheter layer and the resin layer, the resin layer being comprised of a resin composition different from the composition forming the catheter layer;

mounting a hub to the proximal end of the catheter body to form a catheter;

sealing the catheter with a packaging material which exhibits barrier properties to bacteria; and electron-beam sterilizing the catheter sealed with the packaging material through use of electron-beam irradiation.

2. The process according to claim 1, wherein the resin composition forming the resin layer is more flexible than the composition forming the catheter layer.

3. The process according to claim 1, wherein the composition forming the catheter layer is formed by extruding the composition onto a mandrel.

4. The process according to claim 1, wherein the composition forming the catheter layer includes both ETFE and PTFE in a mass ratio of 90:10 to 80:20.

5. A process for producing a catheter comprising:

mixing ETFE and PTFE in a mass ratio of from 99:1 to 45:55 to form a mixture;

forming the mixture into a tubular body;

forming a reinforcement layer and a resin layer on said tubular body to form a catheter configured to be positioned in a lumen of a living body;

sealingly packaging the catheter to produce a packaged catheter; and sterilizing the packaged catheter with electron beam irradiation.

6. The process according to claim 5, wherein the forming of the reinforcement layer involves forming the reinforcement layer between the tubular body and the resin layer.

7. The process according to claim 5, wherein the resin layer is composed of a resin composition different from a composition forming the tubular body.

8. The process according to claim 7, wherein the resin composition forming the resin layer is more flexible than the composition forming the tubular body.

9. The process according to claim 5, wherein the forming of the mixture into the tubular body comprises extruding the mixture onto a mandrel.

10. The process according to claim 9, wherein the mixture is baked while on the mandrel.

11. The process according to claim 5, wherein the mixture includes organic material different from and in addition to the PTFE and ETFE.

12. A process of manufacturing and packaging a catheter comprising:

manufacturing a catheter comprised of a catheter layer made of a composition that includes both ETFE and PTFE in a mass ratio of 99:1 to 45:55, the catheter being configured to be positioned in a lumen of a living body;

sealing the catheter with a packaging material which exhibits barrier properties to bacteria;

electron-beam sterilizing the catheter sealed with the packaging material through use of electron-beam irradiation.

13. The process according to claim 12, wherein the composition includes organic material different from and in addition to the PTFE and ETFE.

14. The process according to claim 12, wherein the manufacturing of the catheter comprises forming a reinforcement layer outside the catheter layer so the reinforcement layer overlies the catheter layer.

15. The process cording to claim 12, wherein the manufacturing of the catheter comprises forming a forming a resin layer outside the catheter layer so the resin layer overlies the catheter layer.

16. The process according to claim 12, wherein the manufacturing of the catheter comprises forming a forming a reinforcement layer outside the catheter layer and forming a resin layer outside the reinforcement layer.

17. The process according to claim 16, wherein the resin layer is composed of a resin composition different from the composition forming the catheter layer.

18. The process according to claim 17, wherein the resin composition forming the resin layer is more flexible than the composition forming the catheter layer.

19. The process according to claim 12, wherein the manufacturing of the catheter layer comprises extruding the composition onto a mandrel.

20. The process according to claim 19, wherein the mandrel and the composition extruded onto the mandrel are baked.

* * * * *